United States Patent
Kerr et al.

(10) Patent No.: US 12,148,534 B1
(45) Date of Patent: Nov. 19, 2024

(54) SYSTEM AND METHOD FOR AUTOMATED ENFORCEMENT OF POLICIES

(71) Applicant: Avalon Health Services, LLC, Tampa, FL (US)

(72) Inventors: William Lamar Kerr, Tampa, FL (US); Jason Eric Bush, Citrus Park, FL (US); Michael Adrian Shaffer, Lutz, FL (US)

(73) Assignee: Avalon Heath Services, LLC, Tampa, FL (US)

( * ) Notice: Subject to any disclaimer, the term of this patent is extended or adjusted under 35 U.S.C. 154(b) by 324 days.

(21) Appl. No.: 16/141,459

(22) Filed: Sep. 25, 2018

Related U.S. Application Data (60) Provisional application No. 62/562,525, filed on Sep. 25, 2017.

(51) Int. Cl.
| | | |
|---|---|---|
| *G06Q 40/10* | (2023.01) | |
| *G06N 5/025* | (2023.01) | |
| *G16H 70/20* | (2018.01) | |

(52) U.S. Cl.
CPC ............. *G16H 70/20* (2018.01); *G06N 5/025* (2013.01)

(58) Field of Classification Search
CPC .............................. G06Q 40/08; G06F 9/5005
See application file for complete search history.

(56) References Cited

U.S. PATENT DOCUMENTS

| | | | |
|---|---|---|---|
| 10,007,946 B1* | 6/2018 | Levy | G06Q 30/0631 |
| 2003/0187701 A1* | 10/2003 | Bonissone | G06Q 10/10 706/8 |
| 2015/0106123 A1* | 4/2015 | Amarasingham | G06Q 50/01 705/3 |
| 2015/0363555 A1* | 12/2015 | Studsrud | G16H 40/20 705/2 |
| 2016/0283676 A1* | 9/2016 | Lyon | G06Q 40/08 |

* cited by examiner

*Primary Examiner* — Reginald R Reyes
(74) *Attorney, Agent, or Firm* — Mark H. Whittenberger; Holland & Knight LLP (57) ABSTRACT

A computer-implemented method and a computing system for editing a claim includes receiving, via a processor, a real-time web service call comprising a claim. The claim is relative to health care. A plurality of rules are applied to the claim in response to receiving the claim. A recommendation is generated in response to applying the plurality of rules to the claim. The recommendation is a result of applying the plurality of rules to the claim. The recommendation is sent as a web service response. The recommendation is stored on a memory system in response to generating the recommendation.

20 Claims, 6 Drawing Sheets

SYSTEM AND METHOD FOR AUTOMATED ENFORCEMENT OF POLICIES

RELATED APPLICATION

This application claims the benefit of U.S. Provisional Application No. 62/562,525, filed on 25 Sep. 2017; the contents of which are incorporated herein by reference.

FIELD OF THE INVENTION

The present disclosure relates automated enforcement of policies, and more specifically, to a system and method for automating enforcement of policies.

BACKGROUND

In the health care field, health care providers typically have large volumes of health care claims (herein after "claims") submitted to them daily. In order to evaluate the claims, health care providers typically send their claims to a platform that is capable of managing such claims. The platform may be provided by the health care provider itself or by a third party.

To evaluate the claims, known platforms have utilized batch processing. In batch processing, a high volume of data from the claims can be processed. However, the claims are grouped together by similarities in batch processing. For instance, the claims may be grouped together by the time they were submitted, by a specific event, or by a specific health care code. Because the claims are grouped together, claims are not able to be processed singularly, which results in inefficiency and a long process time then had such claims been processed in real time.

SUMMARY

In one embodiment of the present disclosure, a computer-implemented method for editing a claim may include receiving, via a processor, a real-time web service call comprising a claim. The claim may be relative to health care. A plurality of rules may be applied to the claim in response to receiving the claim. A recommendation may be generated in response to applying the plurality of rules to the claim. The recommendation may be a result of applying the plurality of rules to the claim. The recommendation may be sent as a web service response. The recommendation may be stored on a memory system in response to generating the recommendation.

One or more of the following features may be included. The claim may be associated with an individual in response to receiving the claim. The claim may be sorted into a category in response to receiving the claim. The claim may be received via batch processing. The claim may contain pre-determined data elements. The plurality of rules may be comprised of an exclusion. The plurality of rules may be comprised of editing logic. The plurality of rules may be applied in parallel. The plurality of rules may be applied asynchronously. The recommendation may be selected from a plurality of recommendations. The recommendation may be generated by a hierarchy of logic. The recommendation generated may be a highest ranking recommendation generated by the hierarchy of logic.

In one embodiment of the present disclosure, a computing system including a processor and a memory system may be configured to receive a real-time web service call comprising a claim. The claim may be relative to health care. A plurality of rules may be applied to the claim in response to receiving the claim. A recommendation may be generated in response to applying the plurality of rules to the claim. The recommendation may be a result of applying the plurality of rules to the claim. The recommendation may be sent as a web service response. The recommendation may be stored on a memory system in response to generating the recommendation.

One or more of the following features may be included. The claim may be associated with an individual in response to receiving the claim. The claim may be sorted into a category in response to receiving the claim. The claim may be received via batch processing. The claim may contain pre-determined data elements. The plurality of rules may be comprised of an exclusion. The plurality of rules may be comprised of editing logic. The plurality of rules may be applied in parallel. The plurality of rules may be applied asynchronously. The recommendation may be selected from a plurality of recommendations. The recommendation may be generated by a hierarchy of logic and may be a highest ranking recommendation generated by the hierarchy of logic.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

BRIEF DESCRIPTION OF THE DRAWINGS

The accompanying drawings, which are included to provide a further understanding of embodiments of the present disclosure and are incorporated in and constitute a part of this specification, illustrate embodiments of the present disclosure and together with the description serve to explain the principles of embodiments of the present disclosure.

The figures disclose a system and method for automated enforcement of policies, which is denoted as claim editing in the figures, respectively.

DETAILED DESCRIPTION

Reference will now be made in detail to the embodiments of the present disclosure, examples of which are illustrated in the accompanying drawings. The present disclosure may, however, be embodied in many different forms and should not be construed as being limited to the embodiments set forth herein. Rather, these embodiments are provided so that this disclosure will be thorough and complete, and will fully convey the concept of the disclosure to those skilled in the art.

Figure 1:
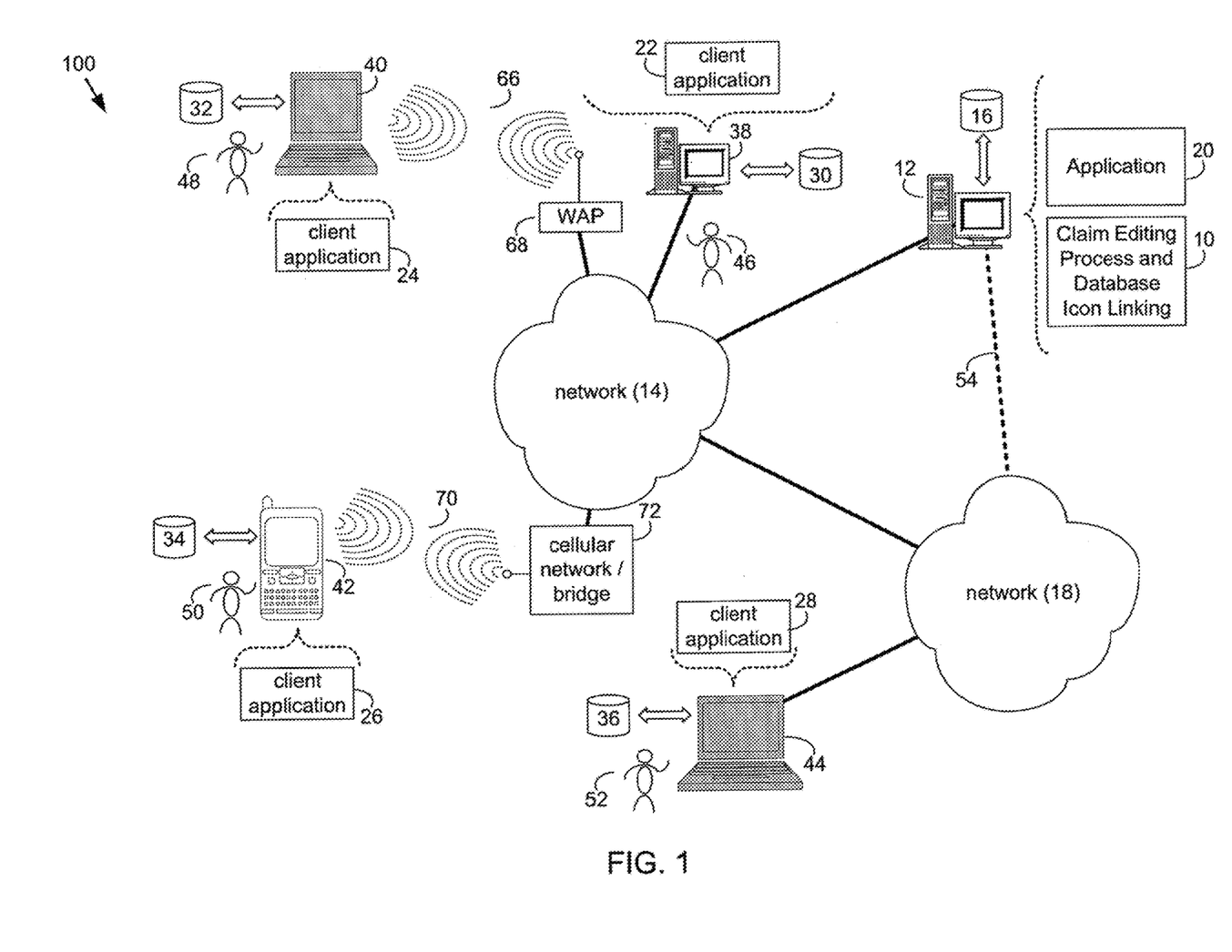
FIG. 1 is a diagrammatic view of system for automated enforcement of policies process in accordance with the present disclosure.

Referring to FIG. 1, there is shown an automated enforcement of policies application 10 (hereinafter "AEPA 10"), denoted as claim editing process 10 in the figures, that may be used for automated enforcement of, for example, health plan policies. The health plan policies may govern coverage or payment, or a combination thereof, of particular items or services of a health plan. AEPA 10 may reside on and may be executed by computer 12, which may be connected to network 14 (e.g., the Internet or a local area network). Examples of computer 12 may include, but are not limited to: a personal computer, a server computer, a series of server computers, a mini computer, and a mainframe computer. Computer 12 may be a web server (or a series of servers) running a network operating system, examples of which may include but are not limited to: ANDROID™, iOS™, Microsoft® Windows® Server; Novell® NetWare®; or Red Hat® Linux®, for example. (Microsoft and Windows are registered trademarks of Microsoft Corporation in the United States, other countries or both; Novell and NetWare are registered trademarks of Novell Corporation in the United States, other countries or both; Red Hat is a registered trademark of Red Hat Corporation in the United States, other countries or both; and Linux is a registered trademark of Linus Torvalds in the United States, other countries or both.) Additionally/alternatively, AEPA may reside on and be executed, in whole or in part, by a client electronic device, such as a personal computer, notebook computer, personal digital assistant, or the like.

The instruction sets and subroutines of AEPA 10, which may include one or more software modules, and which may be stored on storage device 16 coupled to computer 12, may be executed by one or more processors (not shown) and one or more memory modules (not shown) incorporated into computer 12. Storage device 16 may include various types of memory systems. For example, but not limited to, storage device 16 may include: a hard disk drive; a solid state drive, a tape drive; an optical drive; a RAID array; a random access memory (RAM); a read-only memory (ROM). Storage device 16 may include various types of files and file types.

Computer 12 may execute a web server application, examples of which may include but are not limited to: Microsoft IIS, Novell Webserver™, or Apache® Webserver, that allows for HTTP (e.g., HyperText Transfer Protocol) access to computer 12 via network 14 (Webserver is a trademark of Novell Corporation in the United States, other countries, or both; and Apache is a registered trademark of Apache Software Foundation in the United States, other countries, or both). Network 14 may be connected to one or more secondary networks (e.g., network 18), examples of which may include but are not limited to: a local area network; a wide area network; or an intranet, for example.

Computer 12 may execute a wireless communication asset identification application (e.g., application 20). Application 20 may interact with one or more client applications (e.g., client applications 22, 24, 26, 28). Application 20 may be referred to herein as a wireless communication asset identification tool.

AEPA 10 may be a stand-alone application, or may be an applet/application/script that may interact with and/or be executed within application 20. In addition/as an alternative to being a server-side process, AEPA 10 may be a client-side process (not shown) that may reside on a client electronic device (described below) and may interact with a client application (e.g., one or more of client applications 22, 24, 26, 28). Further, AEPA 10 may be a hybrid server-side/client-side process that may interact with application 20 and a client application (e.g., one or more of client applications 22, 24, 26, 28). As such, AEPA may reside, in whole, or in part, on computer 12 and/or one or more client electronic devices. In some embodiments, AEPA 10 and/or application 20 may be independent web applications accessible via the Internet. In some embodiments, AEPA 10 and/or application 20 may be executable applications within a web page or web site accessible via the Internet.

The instruction sets and subroutines of application 20, which may be stored on storage device 16 coupled to computer 12 may be executed by one or more processors (not shown) and one or more memory modules (not shown) incorporated into computer 12.

The instruction sets and subroutines of client applications 22, 24, 26, 28, which may be stored on storage devices 30, 32, 34, 36 (respectively) coupled to client electronic devices 38, 40, 42, 44 (respectively), may be executed by one or more processors (not shown) and one or more memory modules (not shown) incorporated into client electronic devices 38, 40, 42, 44 (respectively). Storage devices 30, 32, 34, 36 may include but are not limited to: hard disk drives; solid state drives, tape drives; optical drives; RAID arrays; random access memories (RAM); read-only memories (ROM), compact flash (CF) storage devices, secure digital (SD) storage devices, and memory stick storage devices. Examples of client electronic devices 38, 40, 42, 44 may include, but are not limited to, personal computer 38, laptop computer 40, mobile computing device 42 (such as a smart phone, netbook, or the like), notebook computer 44, for example. Using client applications 22, 24, 26, 28, users 46, 48, 50, 52 may access application 20 and may allow users to e.g., utilize AEPA 10.

Users 46, 48, 50, 52 may access application 20 directly through the device on which the client application (e.g., client applications 22, 24, 26, 28) is executed, namely client electronic devices 38, 40, 42, 44, for example. Users 46, 48, 50, 52 may access application 20 directly through network 14 or through secondary network 18. Further, computer 12 (e.g., the computer that executes application 20) may be connected to network 14 through secondary network 18, as illustrated with phantom link line 54.

The various client electronic devices may be directly or indirectly coupled to network 14 (or network 18). For example, personal computer 38 is shown directly coupled to network 14 via a hardwired network connection. Further, notebook computer 44 is shown directly coupled to network 18 via a hardwired network connection. Laptop computer 40 is shown wirelessly coupled to network 14 via wireless communication channel 66 established between laptop computer 40 and wireless access point (e.g., WAP) 68, which is shown directly coupled to network 14. WAP 68 may be, for example, an IEEE 802.11a, 802.11b, 802.11g, Wi-Fi, and/or Bluetooth device that is capable of establishing wireless communication channel 66 between laptop computer 40 and WAP 68. Mobile computing device 42 is shown wirelessly coupled to network 14 via wireless communication channel 70 established between mobile computing device 42 and cellular network/bridge 72, which is shown directly coupled to network 14.

As is known in the art, all of the IEEE 802.11x specifications may use Ethernet protocol and carrier sense multiple access with collision avoidance (e.g., CSMA/CA) for path sharing. The various 802.11x specifications may use phase-shift keying (e.g., PSK) modulation or complementary code keying (e.g., CCK) modulation, for example. As is known in the art, Bluetooth is a telecommunications industry specification that allows e.g., mobile phones, computers, and personal digital assistants to be interconnected using a short-range wireless connection.

Client electronic devices 38, 40, 42, 44 may each execute an operating system, examples of which may include but are not limited to Microsoft Windows, Microsoft Windows CE®, Red Hat Linux, or other suitable operating system. (Windows CE is a registered trademark of Microsoft Corporation in the United States, other countries, or both.).

Referring to FIGS. 2-6, various embodiments consistent with AEPA are provided. As will be discussed in greater detail below, AEPA 10 may receive 200, via a processor, a real time web service call comprising a claim. A plurality of rules may be applied 202 to the claim in response to receiving 200 the claim. A recommendation may be generated 204 in response to applying 202 the plurality of rules to the claim, where the recommendation may be a result of applying the plurality of rules to the claim. The recommendation may be sent 206 as a web service response. The recommendation may be stored 208 on a memory system in response to generating 204 the recommendation.

Figure 2:
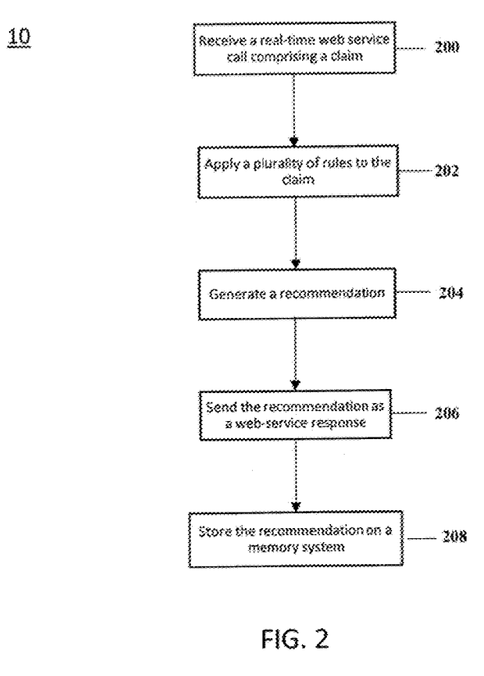
FIG. 2 is a flowchart depicting the automated enforcement of policies system of FIG. 1 according to an embodiment of the disclosure.

Referring to FIG. 2, a flowchart of a computer-implemented method for AEPA is depicted. In one implementation, AEPA 10 may be configured to provide laboratory policy administration through real-time AEPA. AEPA 10 may include one or more claim editors currently provided by a JBoss BPMS KIE technology. For example, a Java call may be placed to DROOLS, which is part of JBoss Business Rules Management System (BRMS). The Java call may then comply with a defined rule decision table into a KIE base container. The defined rule decision table may include may include business rules. The rules may then process flow in KIE. The platform itself may be run on any suitable framework, for example, Linux servers and JBoss applications. Any suitable programming language may be used, including, but not limited to, Java. A significant portion of the code may be embedded in the KIE workflow that supports the AEPA 10.

In some embodiments, AEPA 10 may receive 200, via a processor, a real-time web service call having a health care claim (hereinafter "claim"). For example, AEPA 10 may receive 200 a real-time web service call via a real-time Simple Object Access Protocol (SOAP) or alternative (e.g., RESTful API, Fast Healthcare Interoperability Resources (FHIR), or proprietary web service protocols, etc.) web service call. Receiving 200 the real-time SOAP or alternative web service call may invoke AEPA 10. Typical response time to receiving 200 the real-time web service call may be measured in milliseconds. However, if the real-time web service call is not received, the sender may be notified with an error message. For example, a health care provider's or a third party provider's claim adjudication engine or system (hereinafter "the client") may be used to invoke AEPA 10 by sending a real-time web service call having a claim to AEPA 10. The claim adjudication engine or system may contain pre-determined elements, such as a subset of a claim header and claim line details that are sent from the client and received 200 by AEPA 10. Further, the health care provider or a third party provider may be, for example, Avalon, which supports integration with AEPA 10 via a real-time or batch web service call. However, it will be appreciated that any health care provider or third party provider may generate and send a real-time web service call that may be received 200 by AEPA 10.

In some embodiments, after the claim is received 200 in real-time, a plurality of rules may be applied 202 to the claim. For example, the plurality of rules may include rules based on the subset of the claim header and/or claim line details sent by the claim adjudication engine or system and received 200 by AEPA 10. AEPA 10 may use components of jBoss BPM (jBPM) or other technologies to apply hundreds of thousands of rules to the claim. For example, the plurality of rules applied 202 may include business rules. The business rules may contain an exclusion or editing logic, or both in combination. The rules may take into account numerous factors. For example, in reference to health care, some factors may include, but are not limited to, claim line data including procedure code, modifier, date of service, provider, place of service, diagnosis codes, membership data including patient gender, age, and health plan group, lab claim history including time between tests, cumulative units over a period of time, test incompatibility, etc. Further, the claims may be classified by type to drive AEPA 10 processing and possible exclusion logic. For example, the exclusion logic may contain one or more of the following: as an employer group, line of business, certain Providers or types of claims such as Inpatient or Emergency Room claims that a Health Plan may want to exclude from certain edits for various business reasons. AEPA 10 may be highly configurable to meet medical policy implementations. Though an example is provided relative to health care, the rules applied 202 may be relative to a discipline outside of health care.

In some embodiments, once the plurality of rules has been applied 202 to the claim, a recommendation may be generated 204 by AEPA 10. The recommendation may be generated in real-time. For example, in reference to a health plan, the recommendation may include, but is not limited to, what is appropriate for the health plan provider to pay, whether the services or procedures submitted on the claim should be denied or reduced, etc. Further, the recommendation may be in accordance with established lab policies, which may be taken into account when the plurality of rules is applied 202 to the claim. The lab policies may generally include, for example, medical policies approved by the health care provider or a third party provider, or a combination thereof.

In some embodiments, the recommendation may be generated 204 within sub-second response times in order to support a high volume of claims. Additionally, sub-second response times may support other health care plan processes. For example, the recommendation may be generated 204 within sub-second response times to automate enforcement of "plan policies," which may be recommended policies that a health care provider may adopt. Further, the recommended policies in this example may be of e.g., two general varieties, which may overlap depending on how they are viewed by a client: "medical" policies and "payment" policies. These policies may address laboratory utilization. Additionally, the recommendation generated 204 within sub-second response times may also support other types of medical and payment policies, such as in the context of specialty pharmaceuticals, radiology, ambulance, etc.

Further, AEPA 10 may be used to analyze prospect data by using actual historical paid/denied claims data from a health care policy to reflect the savings opportunity that might be achieved through the health care policy. AEPA 10 may be able to process years of actual historical claim data in a matter of hours. For example, the historical claim data may include: provider adherence to policies, provider steerage and other analytics uses. Edits based on clinical lab results data may also be included. AEPA 10 may be configured to deliver a payment recommendation on potentially any type of health care claim.

After the recommendation is generated 204, the recommendation may be sent 206 as a web-service response. For example, the recommendation may be sent 206 as a web-service response to the client.

In some embodiments, once the recommendation is sent 206, the recommendation may be stored 208 on the memory system. For example, the recommendation may be stored 208 on the memory system, where the memory system may be in association with AEPA 10. Further, the recommendation may be stored 208 for a variety of purposes, such as future analytical analysis. For example, the recommendation may be stored along with the initial request data using e.g., an Amazon Web Services (AWS) SQS queue. In this example, the recommendation and initial request data may be retrieved by an SQL server and stored.

Further, AEPA 10 may be configured to utilize AWS features such as Auto-Scaling, which allows the computing infrastructure to automatically scale up and down based on volume/demand. As a result, AEPA 10 may be able to process very high volumes of data/claims in fractions of the time that it would take to run over a conventional fixed environment infrastructure. Additionally, this allows for the results of AEPA 10 to be stored efficiently to data queues and the persistence of the results may then occur asynchronously, allowing the editor to move on to the next decision. During peak volumes, new servers may be introduced and reduced as needed to support higher loads. Accordingly, AEPA 10 may have the ability to introduce new workflow sub processes to call associated web services.

In another embodiment, the claim may be received by AEPA 10 through RESTFul or batch processing. In batch processing, the client may submit a claim and the claim may be processed with claims having similar elements. For example, the claim may have pre-determined data elements, which can be grouped with another claim sharing some type of similarity.

Figure 3:
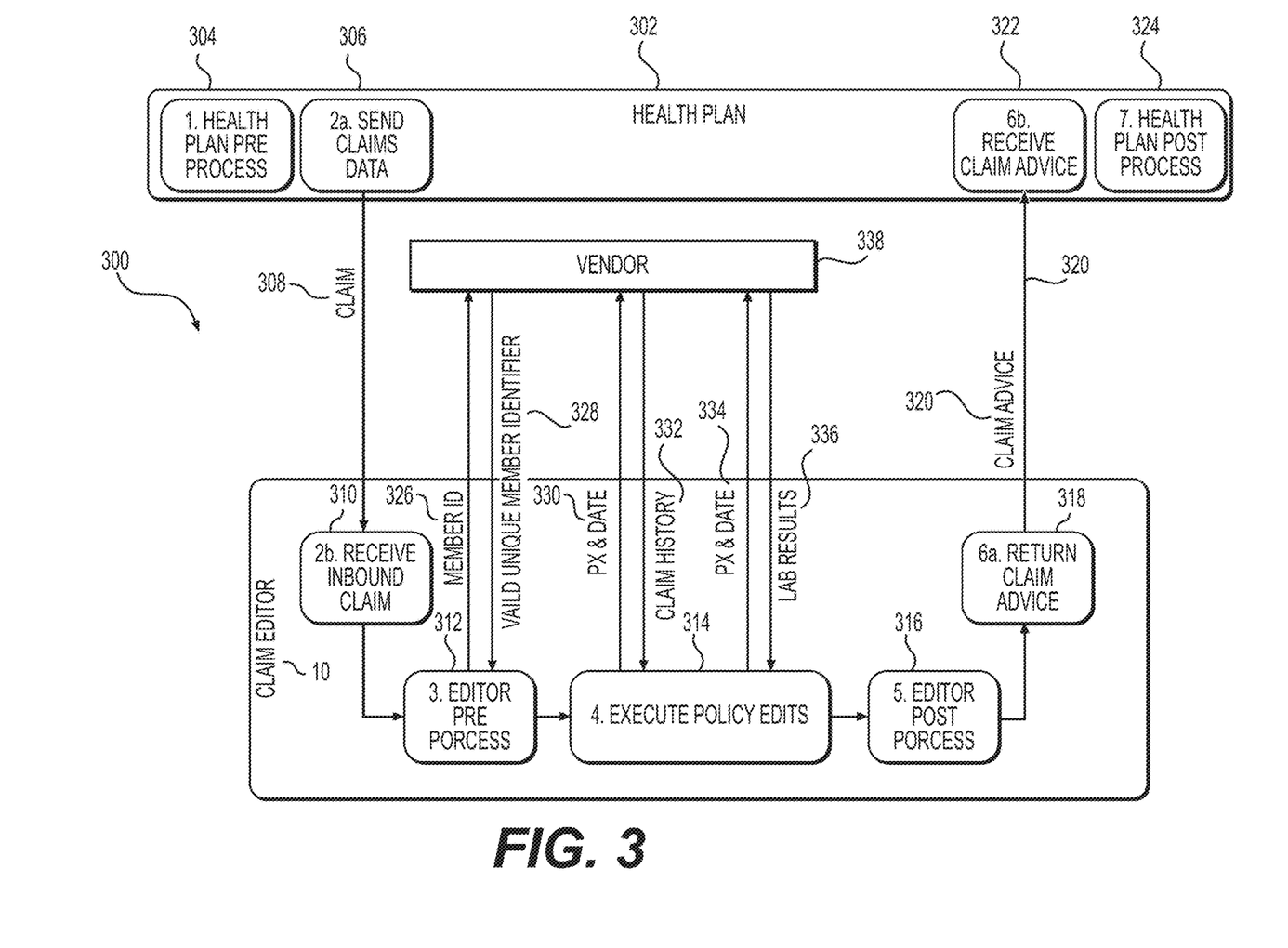
FIG. 3-6 are diagrams of the automated enforcement of policies system of FIG. 1 in accordance with one or more embodiments of the present disclosure; and Like reference symbols in the various drawings indicate like elements.

Referring to FIG. 3, another embodiment of the method and the system for AEPA is depicted in accordance with the present disclosure. The health care provider is depicted as health plan 302. Health plan 302 may execute a health plan pre-process 304, where claim data from a claim may be identified. For example, outpatient laboratory services to be edited by AEPA 10 may be identified. In this example, outpatient laboratory services may refer to laboratory services offered to a patient who is not admitted to a hospital at the time the services are rendered. Health plan 302 may then send 306 the claim data of claim 308 to AEPA 10. The claim 308 is received 310. For example, claim 308 may be received 310 as an inbound claim. AEPA 10 may have an editor pre-process 312. Editor pre-process may perform pre-edit capabilities. For example, editor pre-process 312 may verify member identification (hereinafter "ID") 326 by communicating with the vendor 338. Alternatively, verifying member ID 326 may be bypassed based on instructions sent when claim 308 is received by AEPA 10. Bypassing verifying member ID 326 may allow for a trial claim to be received by AEPA 10. Vendor 338 may then verify member ID 328 to complete editor pre-process 312. Editor pre-process 312 may then send the claim to execute policy edits 314. Execute policy edits 314 may compare the claim data to a plurality of rules. For example, the plurality of rules may refer to health care policy rules, such as a specific medical policy, previous claims, procedure (Px) and date, and/or lab results. In this example, the plurality of rules may be stored on vendor 338. The claim data of claim 308 may be sent to vendor 338. Vendor 338 may send the claim history 332 to execute policy edits 314. Execute policy edits 314 may then apply the plurality of rules to the claim data of claim 308 to generate one or more recommendations. Editor post-process 316 may be applied to the claim data of claim 308 to identify a recommendation. Editor post-process 316 may sort the one or more decisions into a hierarchy. For example, relative to health care, the one or more recommendations generated may be decision codes as to whether or not the claim should be approved, denied, financially adjusted, etc. In this example, editor post process 316 may sort the recommendations into a hierarchy, where the highest ranking, non-excluded decision may be the primary decision identified by editor post-process 316. Specifically, there may be up to eight decision codes that can be ranked, with the highest decision stored separately. However, the decision codes may not be sorted into a hierarchy until exclusions and "pay and educate" decisions (i.e., a modified recommendation needs to be sent to the health plan that can only be determined after all policy rules have been executed) have been noted. Once the exclusions and pay and educate decisions have been noted, the possible decision codes that may be ranked may include: claim line appropriateness (i.e. diagnosis and demographics), prior authorization, date of service procedure code compatibility, frequency, reflexive logic, unit reduction. Further, in this example, a denial decision or a reduction decision marked as "pay and educate" may be ranked lower on the hierarchy than a denial or reduction decision without the pay and educate flag regardless of the denial or reduction reason. Additionally, a denial or reduction decision may be ranked higher in the hierarchy than an excluded denial or reduction regardless of the denial or reduction reason. The denial or reduction decision may have an "X" appended to it if it may not be applied due to an exception. Pay and educate decisions may rank above exclusions. While examples of hierarchical rankings have been provided, it will be appreciated that various hierarchical rankings or rules may be used within the scope of the present disclosure.

In some embodiments, the recommendation identified by editor post process 316 may then be returned 318 as claim advice to health plan 302. For example, relative to healthcare, related policy and medical criteria tags may be returned to health plan 302. Further, a transaction ID may be returned with the recommendation that enables mapping of the recommendation and original claim to AEPA 10. However, a recommendation may include an error message may be returned to health plan 302. The error message may be mapped to AEPA 10. AEPA 10 may also store the recommendation on the memory system as disclosed with regards to FIG. 2. After health plan 302 receives 322 the claim advice, health plan 302 may then execute a health plan post process 324. Health plan post process 324 may link the one or more recommendations together before sending off the recommendations. For example, relative to health care, health plan post-process 324 may link the recommendation, in the form of a decision code, to other decision codes before continuing with adjudication.

Figure 4:
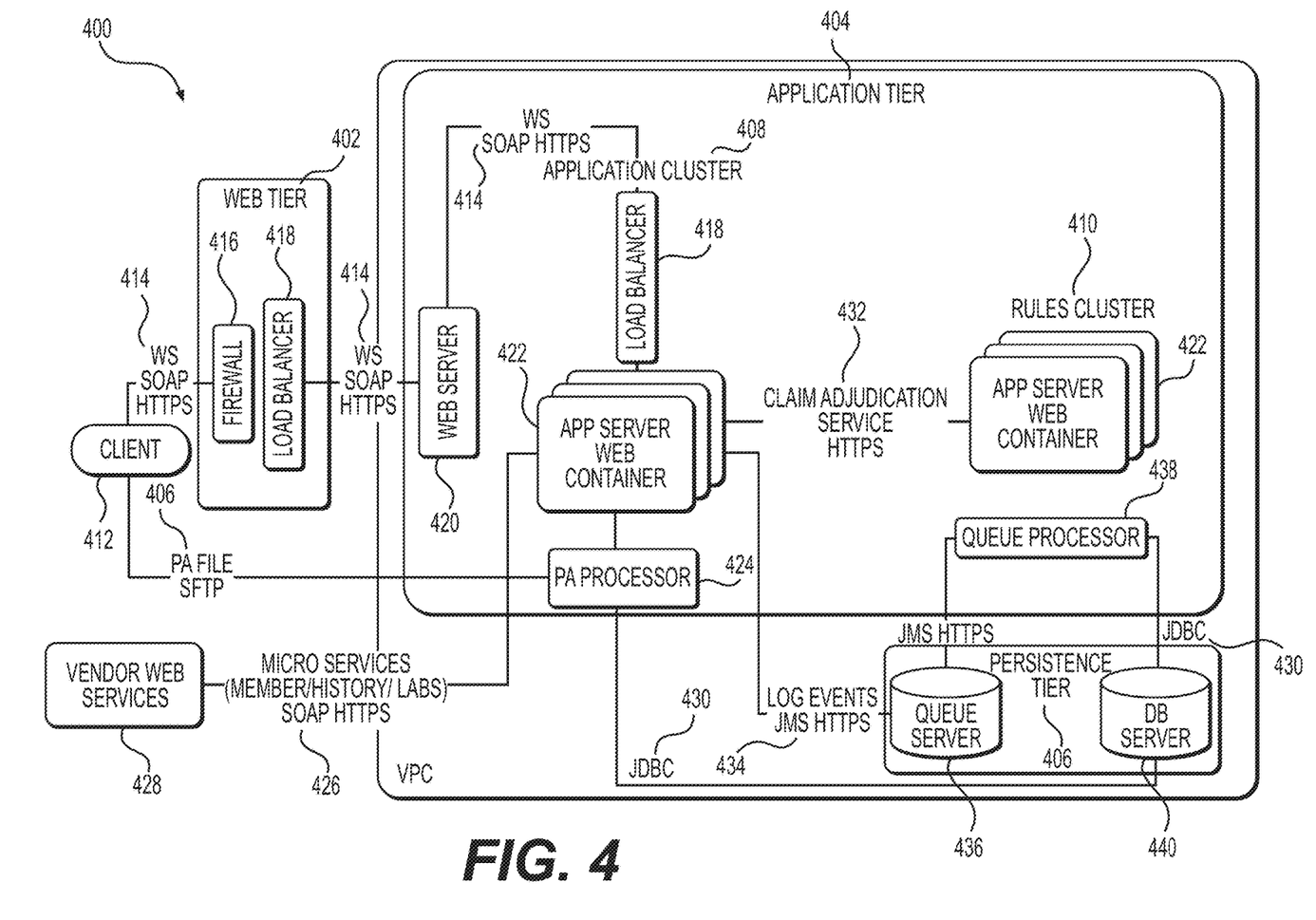

Referring also to FIG. 4, another embodiment of the method and the system for AEPA is depicted in accordance with the present disclosure. A claim may originate at client 412 and be processed through Web tier 402, Application tier 404, and Persistence tier 406. Application tier 404 and Persistence tier 406 may be contained within an Amazon Virtual Private Cloud (VPC). Web tier 402 may have firewall 416 or load balancer 418, or a combination thereof. Application tier 404 may have web server 420, load balancer 418, application cluster 408, Prior Authorization (hereinafter "PA") Processor 424, or rules cluster 410, or a combination thereof. Application cluster 408 may have app server web container 422. Rules cluster 410 may have app server web container 422. Persistence tier 406 may have queue server 436, queue processor 438, or database (DB) server 440, or a combination thereof. Further, vendor web services 428 may provide data to be processed through web tier 402, application tier 404, and/or persistence tier 406.

In some embodiments, when the data from the claim is sent from client 412 to web tier 402, the claim data may pass though firewall 416 or load balancer 418, or a combination thereof. Client 412 may include, for example, a health plan, a managed care organization (MCOs), third party administrators (TPAs), other benefit administrators, or government sponsored plans, or a combination thereof. The claim data may be sent from client 412 to Web tier 402 via a real-time web service call. The real time web service 414 (denoted as "WS" in FIG. 4) call may be a secured SOAP web service call over HTTPS, white listed IP addresses or VPN. After being sent through Web tier 402, the claim data may pass through web server 420 via web service call 414 and load balancer 418. The claim data may then be sent to and processed through application cluster 408 while a plurality of rules are applied to the claim data. The plurality of rules may be sent from rules cluster 410. For example, the plurality of rules may be sent from app server web container 422 via a HTTPS web service call 432. Additionally, Persistence tier 406 may contain, for example, Personal Health Information (PHI) stored in DB server 440. The PHI may be sent to queue processor 438 via Java Database Connectivity (JDBC) 430. The PHI may then be sent from queue processor 438 to queue server 436 via Java Messaging Service (JMS) utilizing an HTTPS web service call 434. The PHI may then be sent from queue server 436 to app server web container 422 via Java Messaging Service (JMS) utilizing an HTTPS web service call 434. Further, vendor web services 428 may contain information that may be sent to app server web container 422. For example, the information sent from vendor web services 428 may relate vendor information such as whether or not the claim was submitted by a member of the health plan, history of the member, clinical laboratory services data. The information sent from vendor web services 428 may be sent via web service call 426. Web service call 426 may a SOAP web service call over HTTPS. The plurality of rules, PHI information, vendor information, and claim data may then be sent from app server web container to PA processor 424 and applied to the claim data. A recommendation may then be generated by PA processor 424. The claim data and recommendation may be sent as PA file 406 using SSH File Transfer Protocol (SFTP) to client 412.

Figure 5:
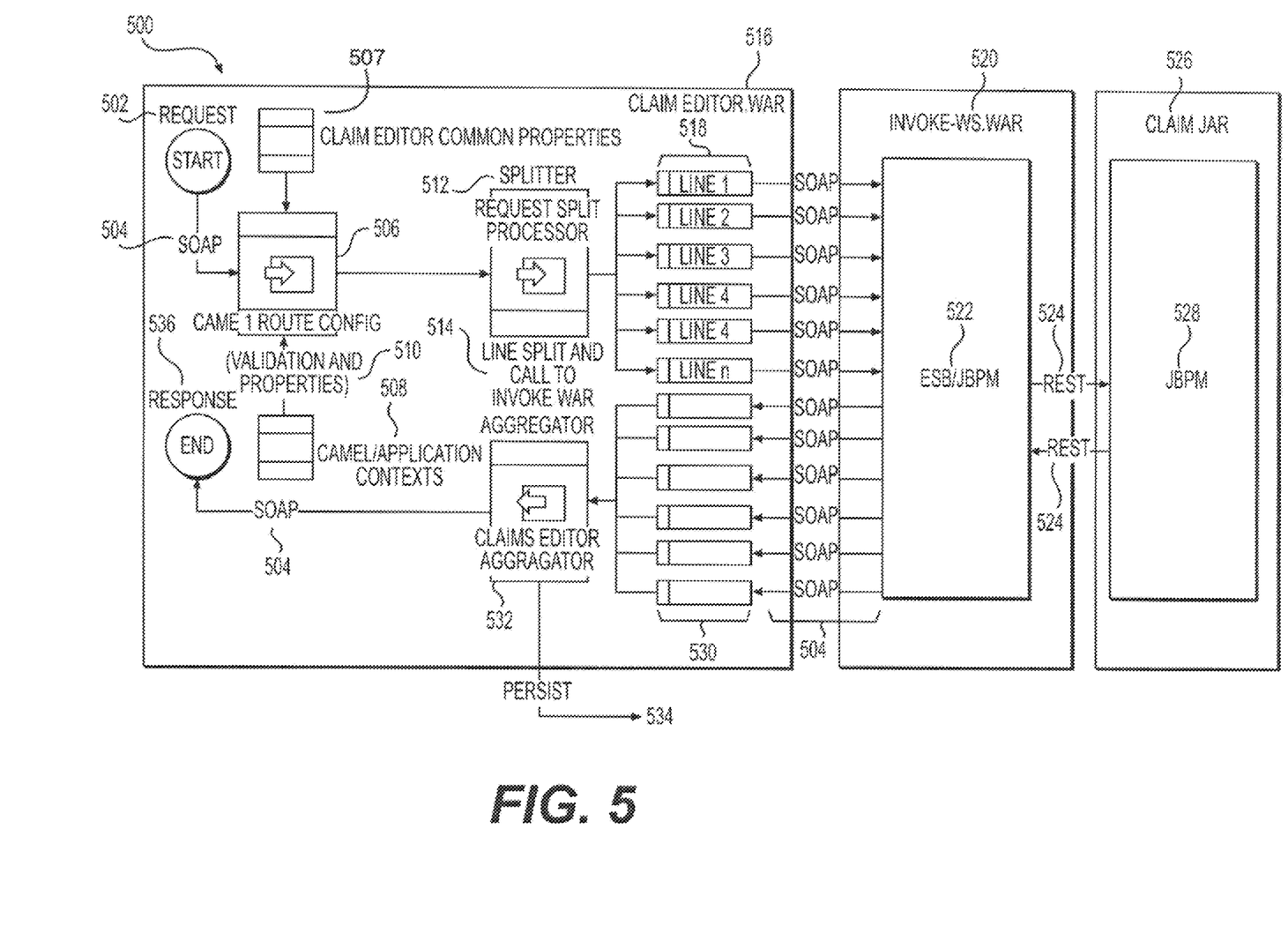

Referring to FIG. 5, another embodiment of the method and the system for AEPA is depicted in accordance with the present disclosure. AEPA 10 may be started with request 502. Request 502 may be a real-time web service call. Once request 502 is received with a claim having claim data, the claim data may be sent to Camel Router 506. In Camel Router 506, application common properties configuration file 507 and application contexts 508 may be applied to the claim data in 506. The claim data may then be sent to splitter 512. Splitter 512, for example, may split the claim data into individual claim lines to process them in parallel. Splitter 512 may also place a call to invoke "WAR" to obtain additional data to be used in the editing process. Individual claim lines 518 may then be transferred to AEPA. WAR to apply line level business rules 520. AEPA. WAR may include Enterprise Service Bus (ESB) or Java Business Process Model (JBPM) 522 via a web service call. For example, the web service call may be a SOAP web service call. Once the individual claim lines 518 are transferred, ESB or JBPM 522 may be applied to individual claim lines 518. Individual claim lines 518 may then be received through Soap or RESTFul processing. JBPM 528 may then be applied to individual claim lines 518. Individual claim lines 518 may then be retuned via Soap or RESTFul processing to Invoke-ws.war 520 where ESB or JBPM 522 may be applied. Individual claim lines 518 are then returned as individual claim lines 530. Individual claim lines 530 may then be sent to aggregator 530. Once individual claim lines 530 are aggregated into claim data, a recommendation may be generated. The claim data and recommendation may be sent as web service response 536. For example, the web service response may be a SOAP web service response.

Figure 6:
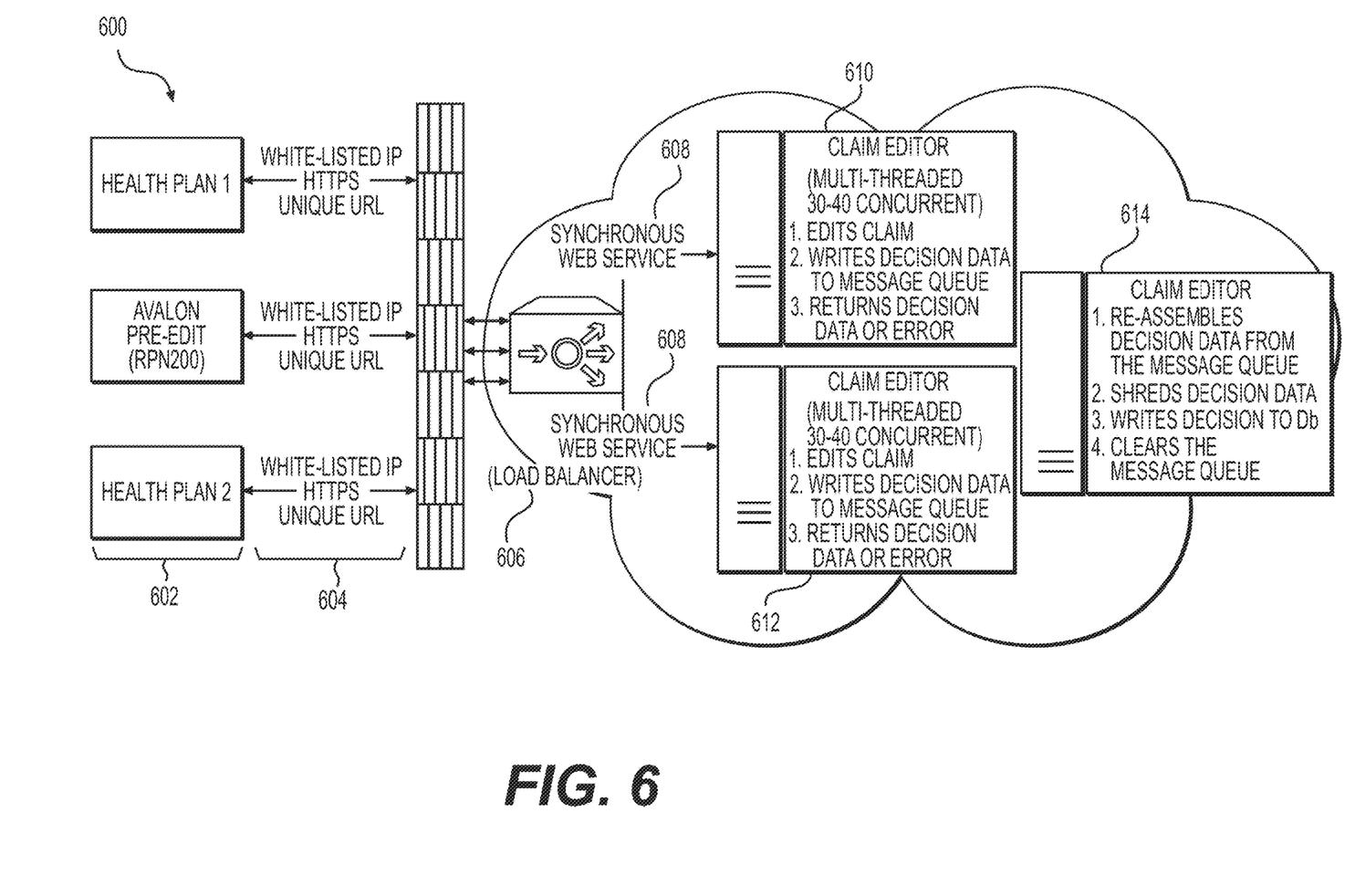

Referring to FIG. 6, another embodiment of the method and the system for AEPA is depicted in accordance with the present disclosure. In this embodiment, health plans 602 may utilize unique channel or unique web path 604. For example, unique web path 604 may include a White-listed IP address using HTTPS and a unique URL. Unique web path 604 may allow for variations in processing a claim each health plan 602 submits. Load Balancer 606 may then manage the load of incoming claims from health plans 602 in order to direct the claims a distinct AEPA engine of AEPA 10. Load balancer 606 may send one or more claims via synchronous web service calls 608 to be evaluated. As shown in FIG. 6, claims 610 and 612 may be edited at the same time, or, rather, in parallel. Claims 610 and 610 may be first edited, a recommendation may be rendered, and the recommendation may then be returned. The results from the editing process may be stored asynchronously, allowing the editing process to continue to the next claim. The recommendation, no matter if the claims are edited in parallel or asynchronously, may be returned to health plans 602 via unique web path 604.

In another embodiment, lab claim results from lab policies may be incorporated into the AEPA 10. In addition, AEPA 10 may allow for the health plan to define requirements that allow for the recommendations to be: tracked for analytical purposes only (without financial impact to the health plan provider or patient), communicated to the provider for education purposes only (without financial impact to the provider or patient), and/or active non-payment recommendations. These payment phases may be configured based on a number of parameters including provider, health plan, line of business or group, and/or dates of service.

Embodiments of AEPA 10 may provide a consistent application of complex edits that may be applied in real-time during high volume health plan claim processing. Embodiments of AEPA 10 may provide the ability to apply complex exclusion logic to support health plan business needs. AEPA 10 may operate using a highly scalable and flexible architecture to flex up and down with demand. For example, flexible, extensible architecture that supports the ability to quickly implement changes to business rules when needed may be utilized by AEPA 10. AEPA 10 may allow for a high rate of auto-adjudication of laboratory claims based on a health plan's laboratory policies. This may result in more accurate and consistent decisions with a shorter claim processing cycle, which is unlike other conventional clinical editors, as other clinical editors do not address lab policies and edits.

In some embodiments, AEPA 10 may provide laboratory policy administration or enforcement, or a combination thereof, through real-time or batch AEPA to reduce over-utilization. Embodiments included herein may establish consistency through standardization and efficiencies through automation that cannot be achieved manually (i.e., by humans) with the volumes and complexities that are involved. AEPA 10 may be used to support a trial claim capability. Providers may be able to validate scenarios to see what the results of the editing process will be in advance of performing services or submitting claims that may end up being edited. For example, relative to health care, this capability may provide a real-time education channel for an ordering physician to validate the appropriateness of a test before a claim is submitted to AEPA 10 that may end up with a denial and service that is not paid.

As will be appreciated by one skilled in the art, the present disclosure may be embodied as a method, system, or computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer readable medium may be a computer readable signal medium or a computer readable storage medium. A computer-usable, or computer-readable, storage medium (including a storage device associated with a computing device or client electronic device) may be, for example, but not limited to, an electronic, magnetic, optical, electromagnetic, infrared, or semiconductor system, apparatus, or device, or any suitable combination of the foregoing. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device. In the context of this document, a computer-usable, or computer-readable, storage medium may be any tangible medium that can contain, or store a program for use by or in connection with the instruction execution system, apparatus, or device.

A computer readable signal medium may include a propagated data signal with computer readable program coded embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber optic cable, RF, etc., or any suitable combination of the foregoing.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present disclosure is described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various implementations of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular implementations only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various implementations with various modifications as are suited to the particular use contemplated.

In one or more embodiments of the present disclosure, a computer program product includes a non-transitory computer readable storage medium having a plurality of instructions stored on it. When executed by a processor, the instructions may cause the processor to perform operations including receiving a first content request from a requesting computing device. Instructions may further be included for associating a user-access identifier from a database with a first portion of data from the first content request based upon, at least in part, a second portion of the data from the first content request. Instructions may further be included for storing the first portion of data from the first content request and the user-access identifier within a memory system. Instructions may further be included for receiving a second content request. Instructions may further be included for generating a user-identifier tag based upon, at least in part, the user-access identifier stored in the memory system, the first portion of data from the first content request, and a first portion of data from the second content request. Instructions may further be included for providing a response to the second content request, the response including the user-identifier tag.

It will be apparent to those skilled in the art that various modifications and variations can be made in the embodiments of the present disclosure without departing from the spirit or scope of the present disclosure. Thus, it is intended that embodiments of the present disclosure cover the modifications and variations provided they come within the scope of the appended claims and their equivalents.

What is claimed is:

1. A computer-implemented method for editing one or more claims comprising:
    receiving, via a processor, one or more real-time web service calls, each call comprising a claim, wherein each claim is relative to a health care plan, wherein each healthcare plan utilizes a unique web-path configured to facilitate variations in processing each claim, wherein the unique web-path includes a white-listed internet protocol (IP) address using hypertext transfer protocol secure (HTTPS) and a uniform resource locator (URL);
    communicating, via a network, with one or more servers belonging to at least one of the health plan provider or a vendor to verify a member ID associated with each claim, wherein a load balancer directs the one or more real-time web service calls for each claim along a corresponding unique web-path;
    applying a plurality of rules to each claim in response to receiving each claim and after verifying the member ID associated with each claim, wherein the plurality of rules include health care policy rules of the health care plan that includes a specific medical policy, wherein applying the plurality of rules to each claim includes
        sending each claim to the vendor,
        receiving claim history from the vendor,
        applying the health care policy rules to each claim based on at least the claim history and the received one or more previous claims, wherein the claim history includes one or more previous claims and the medical procedure associated with each previous claim;
    generating a recommendation, within a sub-second response time, in response to applying the plurality of rules to each claim, wherein the recommendation is a result of applying the plurality of rules to each claim, wherein the recommendation includes at least one of an appropriate amount for the health plan provider to pay or whether each claim should be denied or reduced;
    sending the recommendation as a web service response; and
    storing the recommendation on a memory system in response to generating the recommendation, wherein the memory system includes one or more servers configured to dynamically expand or reduce storage capacity during periods of peak volume.

2. The computer-implemented method of claim 1, further comprising associating each claim with an individual in response to receiving the claim.

3. The computer-implemented method of claim 1, further comprising sorting each claim into a category in response to receiving each claim.

4. The computer-implemented method of claim 1, wherein receiving each claim occurs via batch processing.

5. The computer-implemented method of claim 1, wherein each claim contains pre-determined data elements.

6. The computer-implemented method of claim 1, wherein the plurality of rules comprise one or more of an exclusion and editing logic.

7. The computer-implemented method of claim 1, wherein the plurality of rules are applied in parallel.

8. The computer-implemented method of claim 1, wherein the plurality of rules are applied asynchronously.

9. The computer-implemented method of claim 1, wherein the recommendation is selected from a plurality of recommendations.

10. The computer-implemented method of claim 1, wherein the recommendation is generated by a hierarchy of logic.

11. The computer-implemented method of claim 10, wherein the recommendation generated is a highest ranking recommendation generated by the hierarchy of logic.

12. A computing system including a processor and a memory system configured to perform operations comprising:
    receiving, via a processor, one or more real-time web service calls, each call comprising a claim, wherein each claim is relative to a health care plan, wherein each healthcare plan utilizes a unique web-path configured to facilitate variations in processing each claim, wherein the unique web-path includes a white-listed internet protocol (IP) address using hypertext transfer protocol secure (HTTPS) and a uniform resource locator (URL);

communicating, via a network, with one or more servers belonging to at least one of the health plan provider or a vendor to verify a member ID associated with each claim, wherein a load balancer directs the one or more real-time web service calls for each claim along a corresponding unique web-path;

applying a plurality of rules to each claim in response to receiving each claim and after verifying the member ID associated with each claim, wherein the plurality of rules include health care policy rules of the health care plan that includes a specific medical policy, wherein applying the plurality of rules to each claim includes sending each claim to the vendor, receiving claim history from the vendor, applying the health care policy rules to each claim based on at least the claim history and the received one or more previous claims, wherein the claim history includes one or more previous claims and the medical procedure associated with each previous claim;

generating a recommendation, within a sub-second response time, in response to applying the plurality of rules to each claim, wherein the recommendation is a result of applying the plurality of rules to each claim, wherein the recommendation includes at least one of an appropriate amount for the health plan provider to pay or whether each claim should be denied or reduced;

sending the recommendation as a web service response; and storing the recommendation on a memory system in response to generating the recommendation, wherein the memory system includes one or more servers configured to dynamically expand or reduce storage capacity during periods of peak volume.

13. The computing system of claim 12, further comprising associating each claim with an individual in response to receiving the claim.

14. The computing system of claim 12, wherein receiving each claim occurs via batch processing.

15. The computing system of claim 12, wherein each claim contains pre-determined data elements.

16. The computing system of claim 12, wherein the plurality of rules comprise one or more of an exclusion and editing logic.

17. The computing system of claim 12, wherein the plurality of rules are applied in parallel.

18. The computing system of claim 12, wherein the plurality of rules are applied asynchronously.

19. The computing system of claim 12, wherein the recommendation is selected from a plurality of recommendations.

20. The computing system of claim 12, wherein the recommendation is generated by a highest ranking recommendation from a hierarchy of logic.

* * * * *